United States Patent [19]

Klein et al.

[11] 4,382,782
[45] May 10, 1983

[54] END-CONNECTOR GROMMET DEVICE FOR ORTHODONTIC CHAIN

[75] Inventors: Paul E. Klein, Lake Oswego; Roland M. Anderson, Wilsonville, both of Oreg.

[73] Assignee: Modcom, Inc., Canby, Oreg.

[21] Appl. No.: 391,000

[22] Filed: Jun. 23, 1982

[51] Int. Cl.³ .............................................. A61C 7/00
[52] U.S. Cl. ........................................ 433/18; 433/19
[58] Field of Search ................................... 433/19, 18

[56] References Cited

U.S. PATENT DOCUMENTS 3,997,970 12/1976 Hodgson .............................. 433/19
4,330,271 5/1982 Anderson ............................. 433/19

*Primary Examiner*—Robert Peshock
*Attorney, Agent, or Firm*—Kolisch, Hartwell & Dickinson

[57] ABSTRACT

A rigid grommet-like end-connector device for use with an end of one or more elastomeric, orthodontic, tension-applying chains of the kind having a string of plural, endless, stretchable loops. The device is primarily useful in intermaxillary-type orthodontic applications, where long-term uninterrupted usage is desired, and where it is important to provide a solid wear-resistant attaching structure for the ends of the force-applying elastomer unit. The proposed device significantly expands the utility of currently available orthodontic chains of the type generally mentioned, by permitting plural strands of these chains to be connected in parallel, so-to-speak, both to amplify force-transmission capabilities, and to enhance longevity of effective performance life.

3 Claims, 5 Drawing Figures

END-CONNECTOR GROMMET DEVICE FOR ORTHODONTIC CHAIN

BACKGROUND AND SUMMARY OF THE INVENTION

This invention pertains to an orthodontic connector device, and more particularly, to a rigid, grommet-like end connector device for use with an end of one or more elastomeric orthodontic, tension-applying chains of the kind having a string of plural, endless, stretchable loops.

There are many instances in the practice of orthodontics where it is necessary to apply what are known as intermaxillary forces: for example, to correct the relative positions of the upper and lower jaws in Class II and Class III malocclusions. In these kinds of applications, because of the wide range of relative movement permitted between upper and lower jaws, a force-applying elastomer extending between connection points provided on the jaws can be subjected to extensive stretching and relaxing, and to major abrasive wear at its end connections. What this means, in terms of effective force application between visits to an orthodontist, is that the wearer must be responsible at regular and relatively frequent intervals to replace worn elastomers faithfully. However, experience has shown that such faithful attention is often not paid by a user, and as a consequence, the final desired result of the related orthodontic procedure is delayed.

A general object of the present invention is to provide a unique end-connector device for use with one or more conventional so-called orthodontic elastomer chains, which device, in a simple and practical manner, obviates the problem of end-connection wear, as outlined above, and promotes the use of multiple parallel-connected chain elastomers, if necessary, to provide an overall long-life force-applying assembly which need not be attended to, except in unusual circumstances, between regular visits to an orthodontist.

The device is designed herein primarily for use with conventional elastomer chains, inasmuch as such chains offer an extremely wide range of elastic stretchability, and are particularly well suited to intermaxillary procedures of the type generally set forth above.

According to a preferred embodiment of the invention, which takes the form what is referred to herein as a rigid grommet-like, end-connector device, the same includes first and second eyelet portions which are joined through an offset gooseneck-like expanse, or stretch, formed integrally with the eyelet portions. The first eyelet portion has a body of revolution, with a generally planar circumferential groove that is designed to receive an end loop in one or more chains of the type mentioned. Extending through the first eyelet portion, along the axis of revolution of its body of revolution, is an aperture which is substantially normal to the plane of the groove—this aperture being adapted for attachment to an external orthodontic appliance, such as a hook mounted on a conventional tooth band. The second eyelet portion is radially offset from the first eyelet portion, to one side of the groove just described, with the second eyelet portion including an aperture extending through it along an axis which is generally radial with respect to the axis of revolution of the first eyelet portion, and which generally occupies the plane of the groove in the first eyelet portion. This second-mentioned aperture is adapted threadably to receive an end portion of a chain whose end loop is mounted in the groove. It functions to guide such an end portion away from the end loop, in a manner resisting removal of the loop from the groove, and in a further manner shrouding or encasing such end portion to protect it against abrasive wear.

The device of the invention offers a number of important advantages, which should be clear from a consideration of the proposed construction just set forth. Where a single chain length is deemed adequate for a particular application, use of an end-connector device made in accordance with the invention, at both ends of such a length, provides for extremely low-wear end-connections for the chain length. Where two or more parallel-connected chains are deemed appropriate for the application, the groove in the proposed device accommodates easy attachment of these, and, as in the single-chain-length application just referred to, the end portions of these multiple chain lengths are afforded low-wear end-connections.

These and other objects and advantages which are attained by the invention will become more fully apparent as the description which follows is read in conjunction with the accompanying drawings.

DETAILED DESCRIPTION OF THE INVENTION

Figure 1:
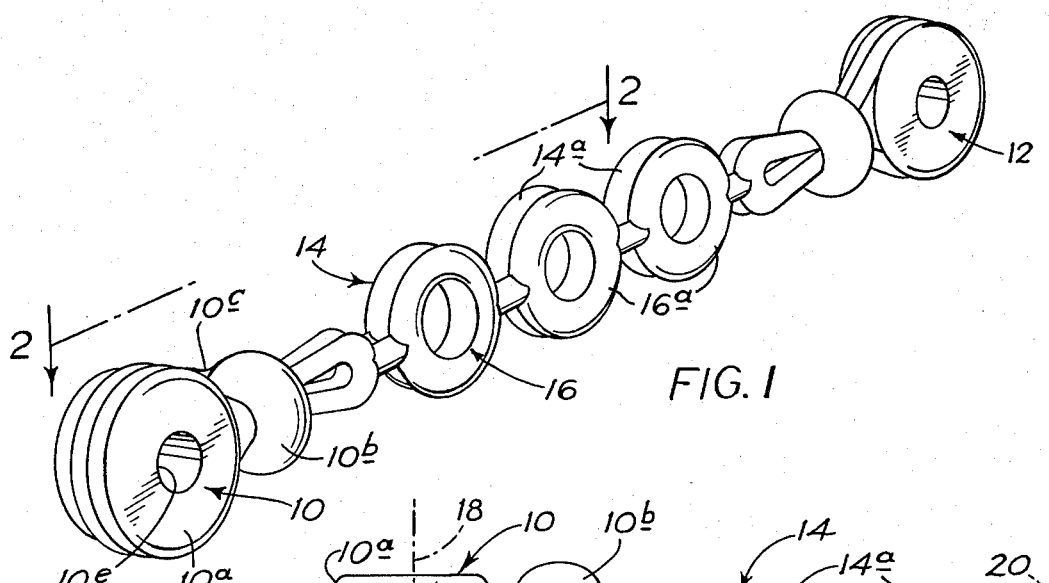
FIG. 1 is a larger than true life perspective view of an orthodontic force-applying assemblage made up of two parallel-cooperating lengths of elastomeric orthodontic chain material, with two end-connector devices, constructed in accordance with the invention, positioned appropriately with respect to two sets of opposite ends of these chains.
Figure 2:
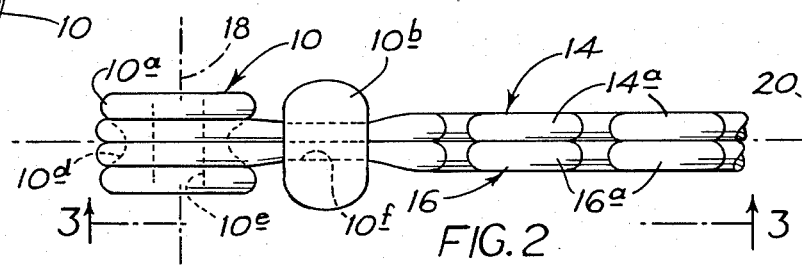
FIG. 2 is a fragmentary view, on about the same scale as FIG. 1, taken generally along the line 2—2 in FIG. 1.
Figure 3:
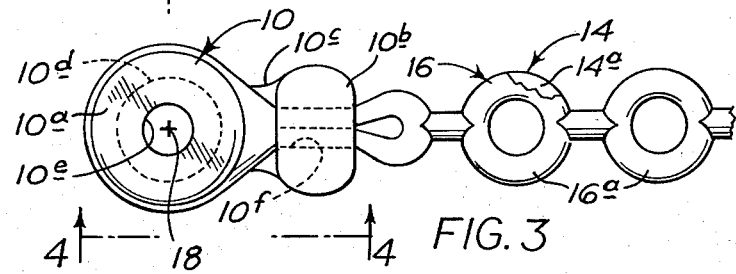
FIG. 3 is a fragmentary view, on about the same scale as FIGS. 1 and 2, taken generally along the line 3—3 in FIG. 2.

Turning now to the drawings, and referring first of all to FIGS. 1–4, inclusive, here there are shown two grommet-like end-connector devices 10, 12, constructed in accordance with the present invention, shown coupled for use, in FIGS. 1–3, inclusive, with a pair of conventional elastomeric orthodontic chain strands shown at 14, 16.

Strands 14, 16 are of a conventional molded construction, formed of a commercially available elastomer which has been used for years in like devices. These strands include plural strand-interconnected stretchable loops, such as the loops shown at 14a, 16a in strands 14, 16, respectively.

The two end-connector devices illustrated are substantial duplicates in construction, and such construction will now be described with reference to device 10.

Device 10 is formed, as by molding, from a suitable rigid plastic material, such as nylon. It includes what are referred to herein as first and second eyelet portions 10a, 10b, respectively, which are formed integrally with an offset gooseneck-like expanse, or stretch, 10c.

Figure 4:
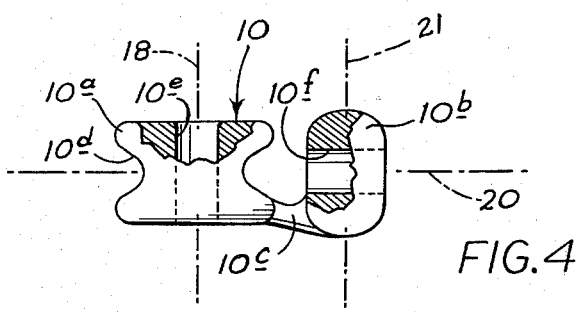
FIG. 4 is a view, also on about the same scale as the other figures so far mentioned, taken generally along the line 4—4 in FIG. 3, showing a single end-connector device made in accordance with the invention, isolated from any chains, and shown with portions broken away to illustrate details of construction.

Eyelet portion 10a, as can be seen clearly, includes a body of revolution which is symmetric with respect to an axis of revolution 18. It has a generally planar circumferential groove 10d, and a central aperture 10e which extends along axis 18, and opens to opposite sides of eyelet portion 10a. The plane of groove 10d is shown at 20 in FIGS. 2 and 4, and substantially constitutes the plane of drawing FIG. 3. Axis 18 is normal to plane 20. Portion 10b also has a body of revolution centered on the axis of aperture 10f, and lying generally in a plane 21 (FIG. 4).

Eyelet portion 10b, through stretch 10c, is radially offset from eyelet portion 10a, and includes another aperture 10f having a central axis which lies within plane 20, and which intersects axis 18 at substantially a right angle.

According to the invention, end-connector devices, like devices 10, 12, are used typically in pairs at opposite ends of one or more strands of orthodontic chain, like chain strands 14, 16. FIGS. 1, 2 and 3 illustrate a typical situation in which two end-connector devices are used in conjunction with two parallel-acting chain strands. As can be seen, each end-connector device is installed by threading the adjacent end loops in the chain strands through the apertures, like aperture 10f, in the "second" eyelet portions, such as portion 10b, with these end loops then snapped around the "first" eyelet portions, like eyelet portion 10a, and received within the associated grooves, like groove 10d.

With both end-connector devices assembled with respect to the selected number of chain lengths, as is illustrated for the two chain lengths in FIGS. 1–3, inclusive, the total assemblage is ready for use.

Figure 5:
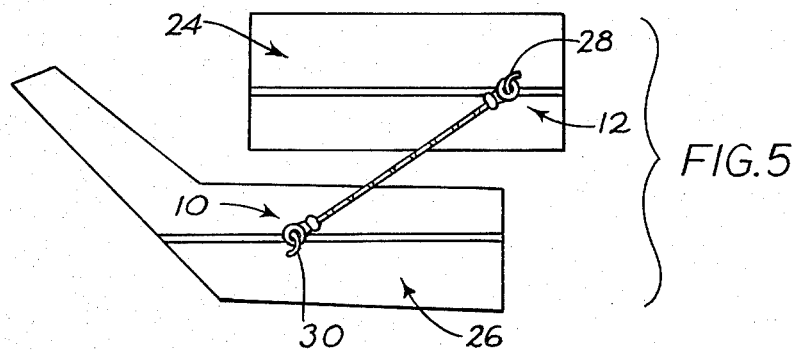
FIG. 5 is a reduced-scale, simplified, schematic view illustrating the device of FIG. 1 mounted in place for a Class II intermaxillary force application.

FIG. 5 illustrates, in a very simplified schematic form, a typical application to correct a Class II malocclusion. Here there is shown, as indicated by bracket 22, a right side view of a person's upper and lower jaws 24, 26, respectively. The front of the mouth is represented at the right side of FIG. 5, and it will be seen that upper jaw 24 is positioned too far forwardly with respect to lower jaw 26. To correct this situation, an intermaxillary-type orthodontic force must be applied to pull the upper jaw rearwardly relative to the lower jaw, and vice versa.

In a typical application, the desired teeth in the upper and lower jaws are banded conventionally, with a pair of front teeth bands, on opposite sides of the upper jaw, carrying mounting hooks, such as hook 28, and with a pair of rear teeth bands, adjacent opposite sides of the lower jaw, carrying mounting hooks, such as hook 30.

Assuming that the assemblage represented in FIGS. 1–3, inclusive, has been decided upon as an appropriate assemblage for correcting the situation shown in FIG. 5, typically, two of these assemblages are prepared as above-indicated, with the open apertures in the "first" eyelet portions of the two and connectors then installed by mounting them on hooks, such as hooks 28, 30. In FIG. 5, the assemblage of FIG. 1 is shown mounted for operation on the near sides of the upper and lower jaws in FIG. 5, with aperture 10e in device 10 caught by hook 30, and with the corresponding aperture in device 12 caught by hook 28. Chain strands 14, 16 then stretch between the upper and lower jaws.

The device of the invention has proven to be extremely satisfactory in providing for long-term, non-replacement-requiring intraoral use, as, for example, between visits to an orthodontist's office. The chain lengths selected, single or plural, offers a great deal of stretchability to accommodate the wide range of relative movement permitted between the jaws. The manners in which the chain length(s)'s end loops are mounted with respect to the end-connector devices, substantially completely obviates disconnection of an end of a strand. Further, because of the construction of what was referred to above as the "second" eyelet portions and the gooseneck stretches in the devices, and because the end-connector devices themselves directly mount on hooks, end abrasion wear in an elastomer chain is also substantially completely avoided. The devices proposed herein are simple and inexpensive to manufacture, and are easy to use. They substantially solve a major problem in the past with respect to required user attendance, which has adversely delayed desired final results.

While a preferred embodiment of the invention has been described herein, it is appreciated that variations and modifications may be made without departing from the spirit of the invention.

It is claimed and desired to secure as Letters Patent:

1. A rigid grommet-like end-connector device for use with an end of one (or plural) elastomeric, orthodontic, tension-applying chains of the kind having a string of plural, endless, stretchable loops, said device comprising a first eyelet portion having a body of revolution with a generally planar circumferential groove designed for encircling receipt of an end loop in such a chain, said portion having an aperture extending along the axis of revolution of said body of revolution, substantially normal to the plane of said groove, adapted for attachment to an external orthodontic appliance, and a second eyelet portion joined to said first eyelet portion, and disposed radially offset therefrom to one side of said groove, with an elongated aperture extending therethrough along an axis which is generally radial with respect to the axis of said body of revolution, and which generally occupies the plane of said groove, said second-mentioned aperture being adapted threadably to receive an end portion of such a chain, and to guide the same away from an end loop in the chain which is received by said groove, in a manner resisting removal of such a loop from the groove.

2. The device of claim 1, wherein said axes intersect and are substantially normal to one another.

3. The device of claims 1 or 2, wherein said first and second eyelet portions are joined through an offset gooseneck-like stretch extrending generally in a plane containing both of said axes.

* * * * *